United States Patent [19]
Norell

[11] Patent Number: 5,441,698
[45] Date of Patent: Aug. 15, 1995

[54] BEVEL CLOSURE AND DEVICE

[75] Inventor: Joyce L. Norell, Boulder Creek, Calif.

[73] Assignee: Beckman Instruments, Inc., Fullerton, Calif.

[21] Appl. No.: 119,466

[22] Filed: Sep. 10, 1993

[51] Int. Cl.6 .............................................. G01N 21/00
[52] U.S. Cl. .............................. 422/58; 422/61; 436/808
[58] Field of Search ................ 422/58, 61; 206/106, 206/823, 470, 477; 436/808

[56] References Cited

U.S. PATENT DOCUMENTS

| | | | |
|---|---|---|---|
| 1,926,299 | 9/1933 | Monk | 206/44 |
| 3,078,031 | 2/1963 | Kauffeld | 229/51 |
| 3,122,301 | 2/1964 | Barr | 229/40 |
| 3,186,623 | 6/1965 | Guyer | 229/51 |
| 3,307,770 | 3/1967 | Wysocki | 229/51 |
| 3,951,332 | 4/1976 | Torbeck | 229/51 |
| 4,225,557 | 9/1980 | Harti et al. | 422/56 |
| 4,285,461 | 8/1981 | Meyers | 229/44 |
| 4,464,552 | 8/1984 | Pawlowski | 206/820 |
| 4,789,629 | 12/1988 | Baker et al. | 422/61 |
| 4,803,048 | 2/1989 | Nason | 422/61 |
| 4,960,565 | 10/1990 | Shurken | 422/61 |
| 4,976,354 | 12/1990 | Levy | 206/456 |
| 5,024,323 | 6/1991 | Bolton | 206/472 |
| 5,100,619 | 3/1992 | Baker et al. | 422/61 |
| 5,119,941 | 6/1992 | Lepie | 206/104 |
| 5,143,210 | 9/1992 | Warwick et al. | 206/45.13 |
| 5,308,580 | 5/1994 | Clark | 422/61 |

Primary Examiner—Lyle A. Alexander
Attorney, Agent, or Firm—William H. May; Gary T. Hampson; Merchant & Gould

[57] ABSTRACT

A closure and device for use with a closure, the closure including a first member having a beveled edge, a second member having an undercut edge, and optionally a base member to which the second member is fixed. The first member is adapted to be received with the beveled edge retained by the undercut edge. A test device may include such a closure and may also include a hinge between the first and second members. Test elements, such as a chromatographic medium and absorbent pads, may be disposed on the first member and/or the base member and may be brought into opposition by closing the first member with the closure.

43 Claims, 5 Drawing Sheets

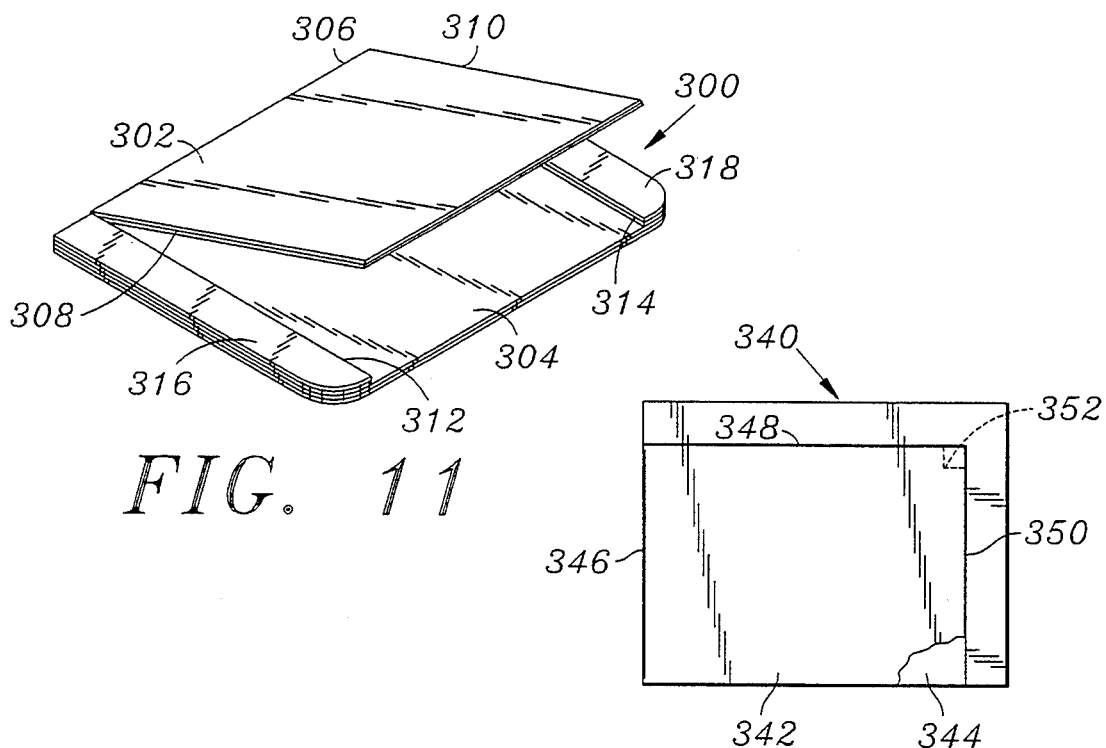
FIG. 11
FIG. 12
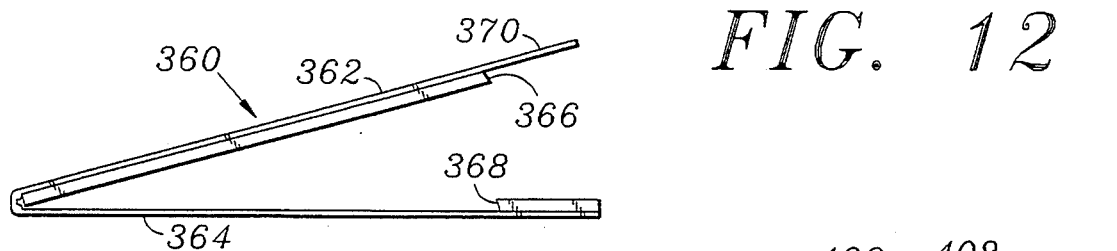
FIG. 13
FIG. 14A
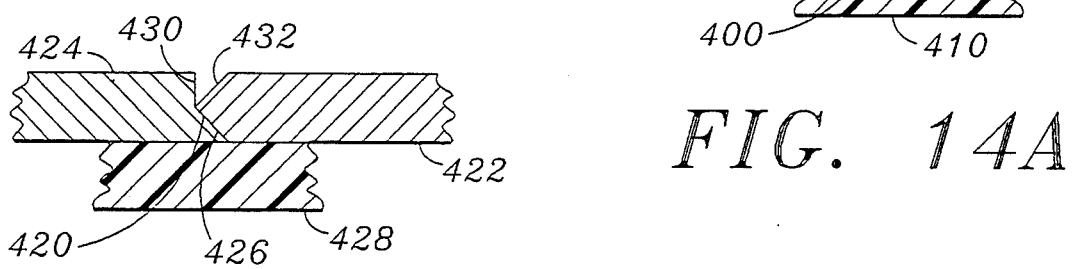
FIG. 14B
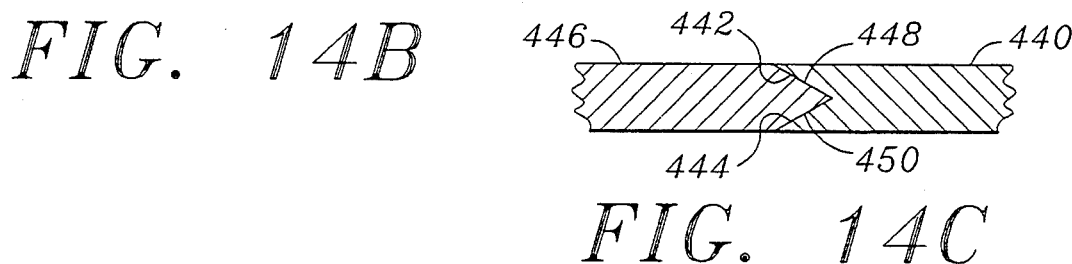
FIG. 14C

BEVEL CLOSURE AND DEVICE

FIELD

The present invention relates generally to the field of closures and devices using such closures.

BACKGROUND OF THE INVENTION

Various closure techniques are known in the art for closing test devices that require a flap or cover to be closed over a base. One simple example is a transfer adhesive that is applied to the base and covered with a peelable tape. The tape is removed and the flap is then pressed against and retained by the adhesive. Typically, however, the adhesive will not thereafter release the flap, and thus the flap may not be again opened without destroying the transfer adhesive closure.

If the flap is to be closed more than once, previously known closure techniques include peelable adhesives carried by a length of tape that is applied over the flap and base. The tape may be peeled back to open the flap and then reapplied to reclose the flap. Additional examples of closure techniques include hook-and-loop fasteners and snap fasteners, where one element of such a fastener is affixed to the flap and the other element is affixed to the base of the device.

These alternatives, however, can be relatively expensive to manufacture, particularly where the elements of hook-and-loop or snap fasteners must be fixed to the flap and base of the device. Further, these closure techniques result in the device being secured at only one point or at most several discrete points between the flap and the base of the device. This can be a particular disadvantage in test devices that require a closing force to be evenly applied between the flap and base of the device.

Thus, there is a need for a closure for use, for example, in testing devices that is relatively simple and inexpensive, allows the device to be opened and closed several times without destroying or substantially degrading the performance of the closure, and can apply a closing force evenly between a device flap and base.

SUMMARY OF THE INVENTION

The present invention satisfies these and other needs. A closure in accordance with the present invention may include a first member having a first angled or beveled edge, a second member having a second angled edge that is supplementary to the first angled edge and means for positioning the first member and the second member to engage the first angled edge and the second angled edge. Alternatively, the second member may be described as having an edge that includes an undercut portion, the first member having an edge including a lip that is adapted to be received in the undercut portion of the second member, and means for positioning the first member and second member to engage the lip within the undercut portion. The first and second members may be planar and a device including a closure of the present invention may include a base member to which is fixed a second member or closure portion, and a first or cover member hinged to the base member.

The first angled edge may define an angle that is less than 90 degrees and, more particularly, between about sixty degrees and eighty-five degrees.

The present invention also contemplates a closeable device including a base member, a cover member, a hinge between the base and cover member, with the cover member including a portion thereof fixed to the base member and a cut formed through the cover member intermediate the fixed portion and the hinge to define an undercut in the portion of the cover member that is fixed to the base member.

The present invention also contemplates a test device incorporating such a closure, the test device further including suitable testing elements such as sample and reagent receiving portions, chromatographic membranes and the like for conducting a test.

The present invention also contemplates a closeable device having two closures of the type described herein, a closeable device where the first portion is removable, and methods of making closeable devices in accordance herewith.

BRIEF DESCRIPTION OF THE DRAWINGS

FIG. 11 is a perspective view of another form of a testing device in accordance with the present invention;

FIG. 12 is another device in accordance with the present invention;

FIG. 13 is a side view of a device in accordance with the present invention, having a covered closure;

FIGS. 14a, 14b, and 14c illustrate alternative forms of a closure in accordance with the present invention.

DETAILED DESCRIPTION

Figure 1:
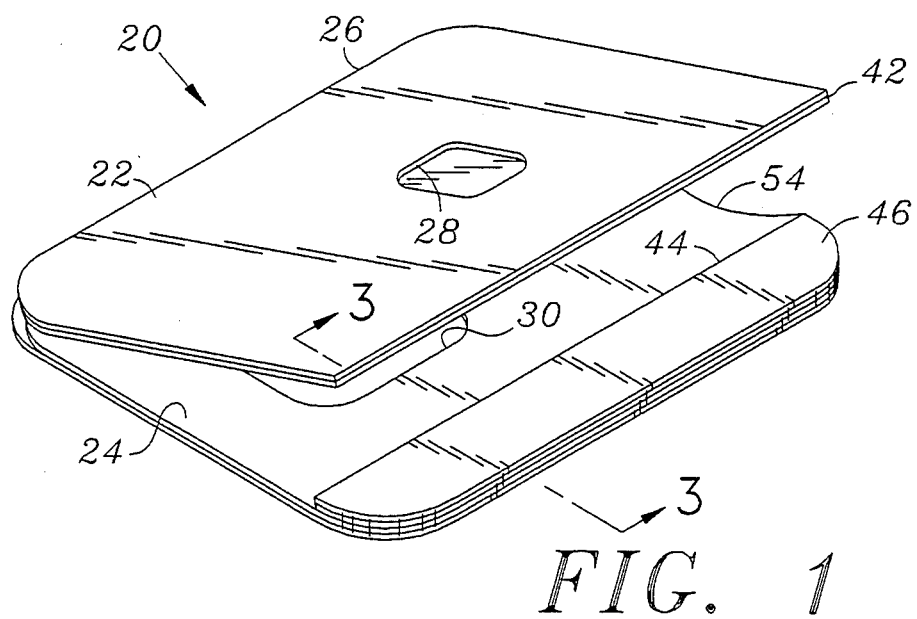
FIG. 1 is a perspective view of a testing device incorporating a closure in accordance with the present invention.
Figure 2:
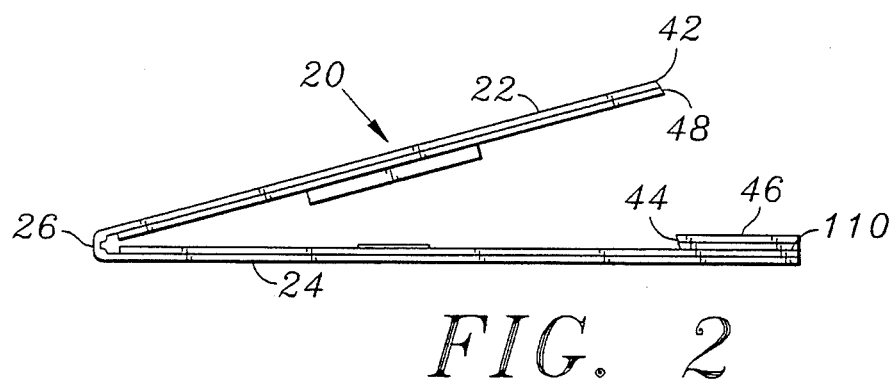
FIG. 2 is a side view of the device of FIG. 1.
Figure 3:
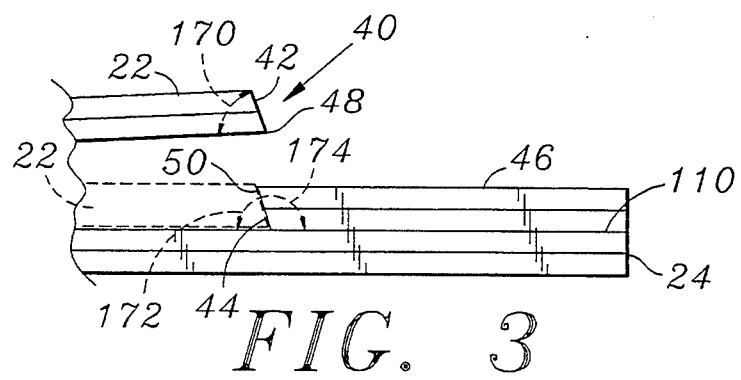
FIG. 3 is a section view taken along line 3—3 of FIG. 1.

With reference to FIGS. 1, 2, and 3, a testing device 20 includes a first planar member in the form of a front panel 22 and a back panel 24. The front panel 22 and the back panel 24 are joined by a hinge 26. The front panel 22 includes a window 28 for observing test results and the back panel 24 includes a well 30 adapted to receive testing elements and reagents as is described more fully below with respect to FIG. 4.

Continuing with FIGS. 1-3, the testing device 20 includes a closure 40 in accordance with the present invention. The closure 40 includes a beveled edge 42 formed at an edge of the front panel 22 opposite to that of the hinge 26 and an undercut edge 44 formed on a closure portion or planar fixed member 46 that is fixed to the back panel 24.

To close the testing device 20 using the closure 40, the front panel 22 is rotated about the hinge 26 such that the cover or front panel 22 and base or back panel 24 are brought together with a protruding lip or corner 48 of the beveled edge 42 brought against the upper surface of the fixed member 46. The front and back panels 22, 24, are urged together, slightly flexing the testing device 20 and in particular the hinge 26, allowing the protruding corner 48 to be displaced beneath an overhanging corner 50 of the undercut edge 44. With the entire length of the beveled edge 42 thus captured by the undercut edge 44 as illustrated by the phantom outline in FIG. 3, the testing device 20 is closed with the front panel 22 in an opposed orientation with respect to the back panel 24. It is seen that the hinge 26 acts as a means for positioning the front and back panels 22, 24 such that the beveled edge 42 is captured, engaged or retained by the undercut edge 44.

Conversely, to open the testing device 20, the front and back panels 22, 24 are urged apart as for example, by holding the fixed member 46 and the back panel 24 between a user's fingers and urging the front panel 22 away from the back panel 24. An outer edge of the front panel 22 can be conveniently accessed via a notch 54 formed in the back panel 24. With opening force applied, the testing device 20 and in particular the hinge 26 again slightly flexes, releasing the beveled edge 42 from the undercut edge 44 and thereby allowing the front panel 22 to be opened with respect to the back panel 24.

Figure 4:
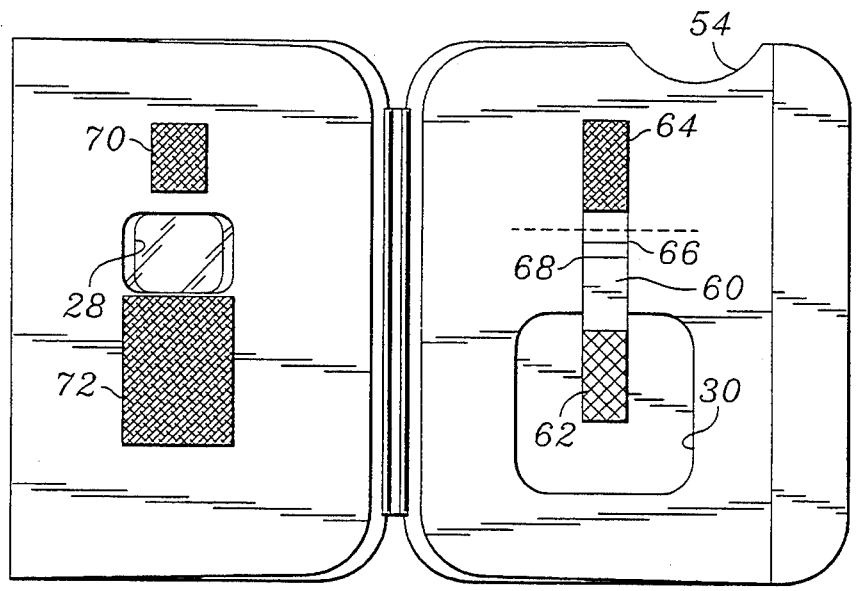
FIG. 4 is a view of the device of FIG. 1 opened to reveal testing structures.

With reference to FIG. 4, the testing device 20 may include testing elements for the analysis of a sample. The testing elements may include with respect to the particular embodiment of FIG. 4 a chromatographic membrane or member 60, a sample application pad 62, and a conductor pad 64 on the inside of the back panel 24. The chromatographic membrane 60 may include first and second lines 66, 68 of immobilized components useful for demonstrating the performance of the testing device 20 and detecting the presence of an analyte in a sample.

The inside of the from panel 22 includes a labeled reagent pad 70 and an absorbent pad 72. The first and second lines of immobilized components 66, 68 are aligned to be visible through the window 28. As so configured, the testing device 20 forms an immunochemical testing device for the detection of, for example, *H. pylori* as is described in U.S. patent application Ser. No. 07/888,831 filed May 27, 1992 in the name of Howard M. Chandler, entitled, "Assay Device" and which is assigned to the same assignee as the present invention, all of which is incorporated herein by reference.

Figure 5:
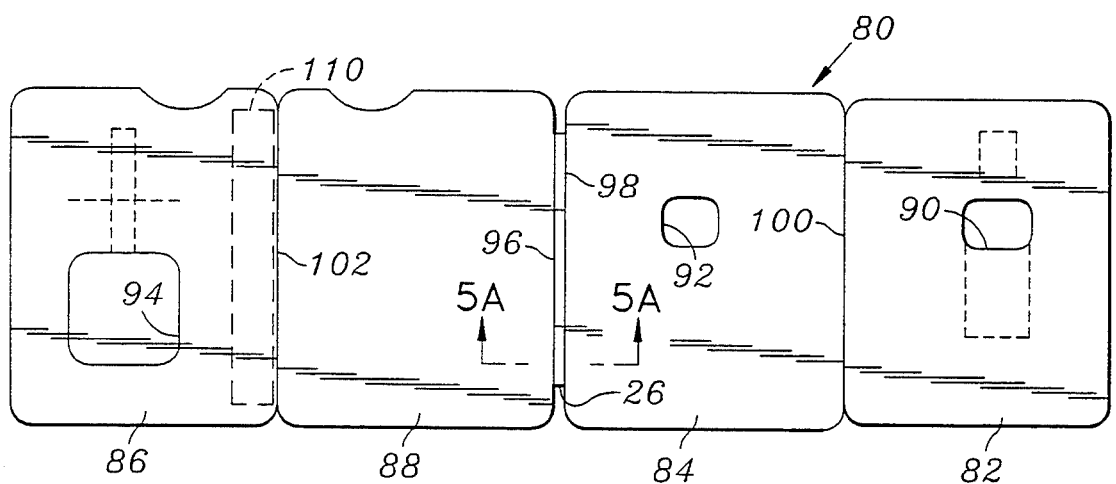
FIG. 5 is a blank from which the device of FIG. 1 may be formed.

Preferably, the testing device 20 is made of paperboard or fiberboard, and is preferably solid bleached sulfite (SBS) paperboard, approximately 0.024 inch thick. The material may be cut to form a blank 80 (FIG. 5). The blank 80 includes a first front panel portion 82 and a second front panel portion 84, as well as a first back panel portion 86 and a second back panel portion 88. The window 28 is formed by first and second openings 90, 92 formed in the first and second front panel portions 82, 84. Similarly, the well 30 is formed by a third opening 94 formed in the first back panel portion 86. Two parallel two-point crease rules 96, 98 (FIG. 5A) are approximately two points apart and aid in forming the hinge 26, an overall distance 97 from the outside edges of the creases rules 96, 98 accordingly being about six points. As an alternative, a six point crease rule 99 (FIG. 5B) can replace the two crease rules of FIG. 5A. Other crease rule widths may be used according to the needs of the particular hinge that is to be formed.

A first cut or score line 100 is cut into the surface of the blank 80 between the first and second front panel portions 82, 84 to aid in forming a sharp fold line between the first and second front panel portions 82, 84. A similar second cut or score line 102 is cut into the surface of the blank 80 between the first and second back panel portions 86, 88.

The blank 80, with the openings 90, 92 and 94, and score lines 100, 102 are preferably die cut and formed all in a conventional fashion.

With the blank 80 formed, the first and second front panel portions 82, 84 are folded along the first score line 100, bringing the first and second front panel portions 82, 84 together. A piece of clear plastic window material may be disposed between the first and second front panel portions 82, 84, thus providing a clear plastic material (not shown in FIG. 5) within the window 28. Preferably, the first and second front panel portions 82, 84 are glued together. Similarly, the first and second back panel portions 86, 88 are folded along the second score line 102 and are glued together.

The various testing elements such as those described with respect to FIG. 4 are applied to the testing device. An adhesive 110, shown in cross section in FIG. 3 and shown in outline form in FIG. 5, is applied to the first back panel 86 proximate the position where the closure is to be formed (as is described herein below). The blank 80 is then folded along the hinge 26 and the front and back panels 22, 24 are pressed together, particularly along the adhesive 110, placing the applicable test elements in opposition.

Figure 6:
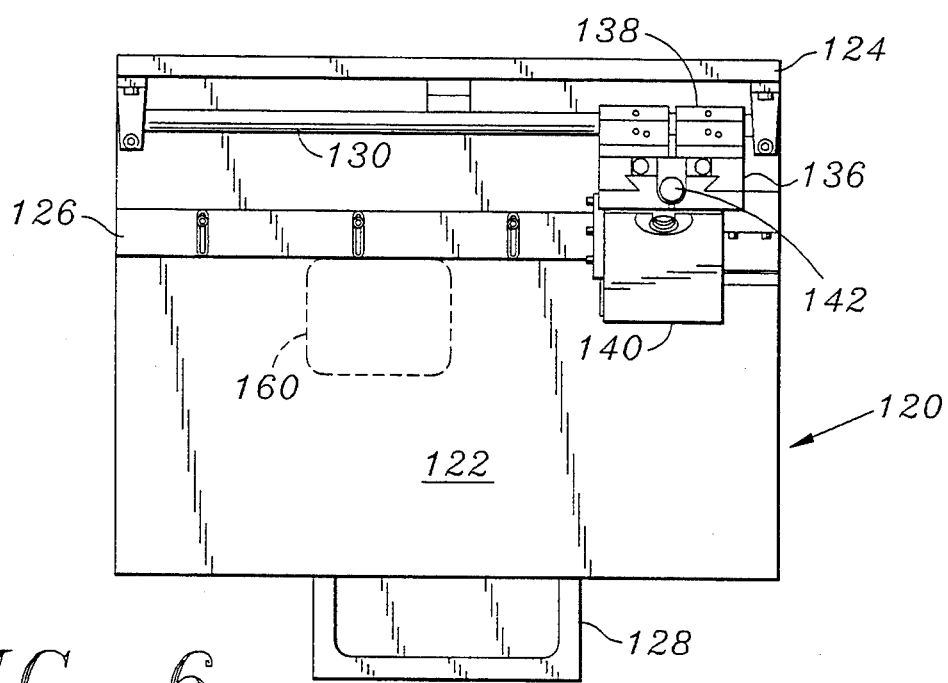
FIG. 6 is a top view of a bevel or closure cutter suitable for forming the closure of the device of FIG. 1.
Figure 7:
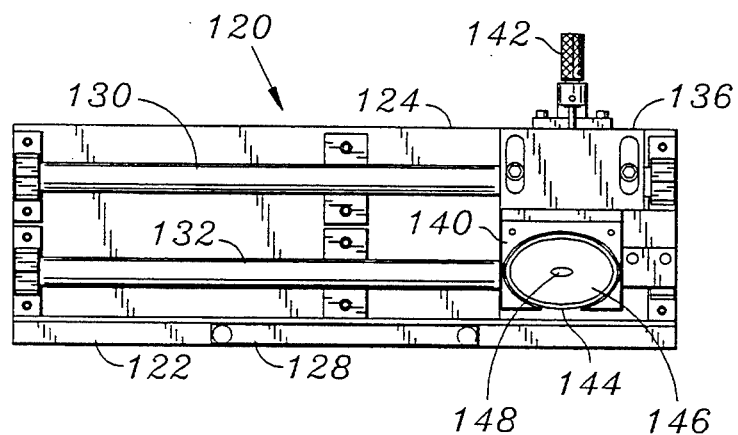
FIG. 7 is a front view of the cutter of FIG. 6.
Figure 8:
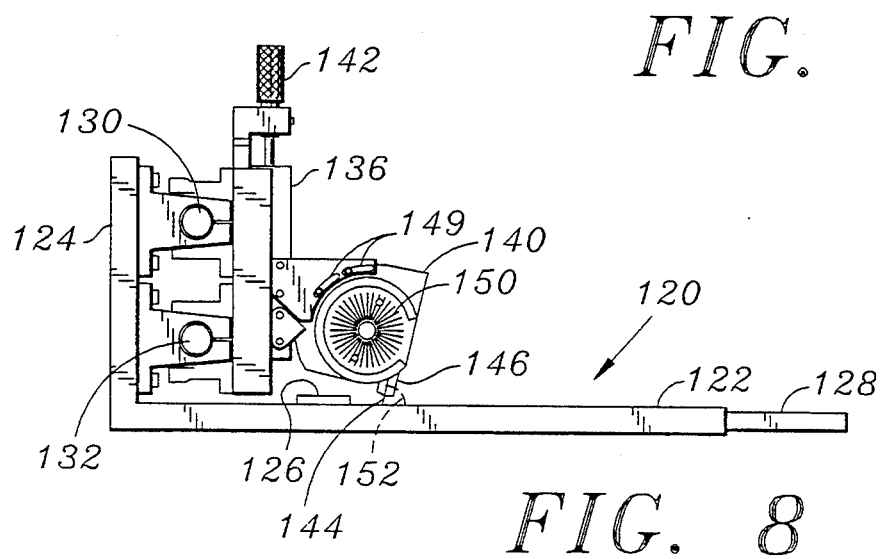
FIG. 8 is a side view of the cutter of FIG. 6.

To form the closure 40, an angled cut is made in the front panel 22. In the embodiment disclosed herein, a bevel cutter 120 as illustrated in FIGS. 6–8 is used to form such a cut. The bevel cutter 120 includes a base 122 and a vertical back member 124. The base 122 includes an adjustable edge guide or straight edge 126 and a handle 128. Mounted to the back plane 124 are two linear rails 130, 132 which in turn carry and support a cutting head 136.

The cutting head 136 includes a linear bearing portion 138 that is supported and guided by the linear rails 130, 132. The linear bearing portion 138 in turn supports a blade assembly 140. A vertical adjustment knob and screw 142 allows vertical adjustment of the blade assembly 140 with respect to the linear bearing portion 138.

The blade assembly 140 carries a rotary blade 144 within a rotary blade holder 146. The rotary blade holder 146 rotates about a support 148. The rotary blade 144 is preferably a double bevel buffed lark blade available from a Blade Tech, Inc. and has an outer diameter of 62 mm. and a thickness of 0.012 inch. The blade assembly 140 may be adjusted to vary the angle of the rotary blade 144 with respect to the base 122 by loosening adjustment screws 149 and the angle may be gauged by means of an angle selection gauge 150.

Although a double bevel rotary blade 144 is described herein, it is to be appreciated that a single bevel blade may also be used to make the required cut in forming a closure such as the closure 40. Further, although the bevel cutter 120 is a manually operated device and suitable for cutting one or relatively few devices at a time, the bevel cutter 120 may be enlarged to allow a larger number of devices to be cut at one time and the cutting head may be moved by suitable means such as a pneumatic cylinder or an electric motor. Also, automated cutting means may be used to cut and thus form a closure in accordance with the present invention with sheet fed or web fed stock, and other culling means such as a straight edge blade or laser, could be employed to form a cut.

To form the closure 40, the testing device 20 is placed on the base 122 as shown by outline 160 (FIG. 6) with the front panel 22 up and the adhesive 110 proximate the straight edge 126. The vertical adjustment knob and screw 142 are adjusted such that the depth of the cut formed by the rotary blade 144 is through the front panel. The angle of the rotary blade 144 is adjusted to the appropriate angle, which in the embodiment disclosed herein is an angle 152 of less than ninety degrees and, for the device and for the material disclosed here, preferably between about sixty degrees and eighty-five degrees, or between about five degrees and thirty degrees from vertical. A preferred angle is about seventy-two degrees, or eighteen degrees from vertical.

With the testing device 20 in place, as shown by the outline 160, the testing device 20 is held firmly against the guide 126 and the cutting head 136 is moved along the linear rails 130, 132 parallel to the edge of the guide 126, thus cleanly forming a cut through the front panel 22 proximate but not over the adhesive 102, and thereby defining the closure 40 and the fixed member 46.

In particular, the beveled edge 42 (FIG. 3) and the undercut edge 44 are formed, defining a bevel angle 170 and an undercut angle 172 equal to the angle set by the rotary blade 144. Thus, the bevel angle 170 and undercut angle 172 are equal, and are less than ninety degrees and may be between about sixty to eighty-five degrees, and for the test device 20, about seventy-two degrees. The undercut angle 172 is supplementary to a fixed member angle 174 formed by the fixed member 46, that is, the undercut angle 172 and the fixed member angle 174 together total one hundred eighty degrees. Thus, the bevel angle 170 and the fixed member angle 174 are likewise supplementary.

In determining the angle of the cut made to form the closure 40 or other closures in accordance with the present invention, factors to be considered include the degree of hold desired when the beveled edge 42 is retained under the undercut edge 44, the thickness of the members or panels that form the beveled and undercut edges, the amount of internal pressure to be applied between opposing test elements carried within a testing device utilizing the closure, hinge design (if a hinge is employed in the device), and the material from which the device is made. In general, any angle less than ninety degrees may be operable and thus within the scope of this invention, provided that the protruding comer 48 is capturable beneath the overhanging comer 50 to thus close the testing device 20, and that the beveled edge 42 can be released from the undercut edge 44 to open the device 20.

Preferably, the adhesive 110 is near the closure 40, and preferably as close as reasonably feasible to prevent gaping or bowing between the fixed member 46 and the back panel 24 as the testing device 20 is opened, pulling the beveled edge 42 from beneath the undercut edge 44. Such bowing may, for example, deform the fixed member 46, and thus varying the closed force applied between opposing testing elements.

With the testing device 20 formed from SBS, it is preferred that the moisture content of the SBS material is fixed or stabilized prior to the formation of the closure 40 by means of the bevel cutter 120. This may be accomplished, for example, by placing the device in a vacuum chamber. Preferably the moisture content of the testing device 20 is stabilized at approximately one percent prior to the formation of the closure 40, although other moisture contents are also possible and will yield a functioning closure in accordance with the present invention. It is to be clearly understood that the closure of the present invention is operable without the moisture content of the testing device 20 being stabilized prior to forming the closure 40. However, moisture stabilization is preferred (although not necessary or required) to provide a more predictable operation of the closure 40 by equalizing and distributing stresses throughout the device before the cut is made and thus decreasing the likelihood of improperly aligned edges 42, 44.

With the closure 40 formed as just described, the testing device 20 may be packaged in a hermetically sealed envelope (not shown) for storage and transportation prior to use.

In use, the device is removed from its protective envelope (note shown) and is opened as described above. A buffer is added to the labeled reagent pad 70 and a sample that may contain *H. pylori* is applied to the sample application pad 62. After a time sufficient to allow the sample to flow through the chromatographic membrane 60 toward the conductor pad 64 and during which any *H. pylori* antigen or antibody (depending of the analyte of interest) is bound to the first line of immobilized component 66, the device 20 is closed by means of the closure 40 as is described above. The absorbent pad 72 is placed into contact with the sample application pad and the reagent application pad is placed into contact with the conductor pad 64. The flow of liquid in the chromatographic membrane is accordingly reversed, and labeled reagent flows through the chromatographic membrane from the labeled reagent pad 70 and the conductor pad 64 toward the sample application pad 62 and the absorbent pad 72. Any immobilized analyte bound to the first line of immobilized component 66 in turn immobilizes labeled reagent, producing a colored line. Further, the labeled reagent is also bound to the second line of immobilized component 68 to demonstrate test device 20 operability. The results of the test are observed through the window 28.

Figure 5A:
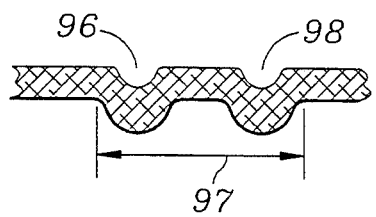
FIG. 5A is a section view of the hinge portion of the blank of FIG. 5 taken along line 5A—5A thereof.
Figure 5B:
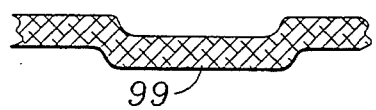
FIG. 5B is a section view of an alternative hinge portion useful in the device of FIG. 1.

The hinge structures illustrated in the cross section embodiments of FIGS. 5A and 5B, and preferably the structure of FIG. 5B, provide stable and consistent hinges 26 that suitably align the beveled edge 42 with the undercut edge 44. It is to be appreciated that if the front panel 22 is offset by, for example, instability of the hinge 26, and the beveled edge 42 moves away from the undercut edge 44, sufficient movement of this nature will prevent the protruding comer 48 from engaging the overhanging comer 50 and cause the closure 40 to fail.

Conversely, if the front panel 22, with the device 20 in its open state, is offset such that the protruding comer 48 substantially overlaps the fixed member 46, it is likely that closing pressure applied to the front and back panels 20, 24 will not engage the closure 40.

Thus, the relatively stable hinge designs of FIGS. 5A and 5B and particularly of FIG. 5B provide two forms of suitable hinges for the present invention. Such designs also enable the distance from the front panel 22 to the back panel 24 to be controlled when the testing device 20 is in its closed condition by varying the distance between the parallel crease rules 96, 98 of FIG. 5A or the overall width of the single wide crease rule 99 of FIG. 5B. This is particularly advantageous for accommodating various thicknesses of testing elements contained within the testing device 20 and also accommodating the amount of pressure that is applied between opposing testing elements as may be required by the characteristics of the testing element materials and the like.

Other hinge designs, such as a rounded hinge, may be similarly suitable and will be apparent to those skilled in the art without undue experimentation.

With the present device of FIG. 1, the length of the closure 40 of the device of FIG. 1 may be, for example, approximately 3 inches, although the size of a device employing a closure in accordance with the present invention may, of course, be adapted over a wide range according to the particular needs.

The width of a testing device in accordance with the present invention and particularly the width of, for example, the front panel 22 (between the closure 40 and the hinge 26) may be varied according to the needs of the testing elements disposed within the testing device. For example, the chromatographic membrane 60 and related testing elements on the front and back panels 22, 24 may be collectively moved toward or away from the closure 40.

It is also to be appreciated that although the closure 40 of the testing device 20 is shown as running the entire length of the device, only a portion of the front panel 22 edge could be formed to define the closure 40 as the needs of the testing device 20 dictate and, further, the length of the front panel 22 (the dimension parallel to the closure 40) need, of course, not correspond to the entire length of the back panel 24 as illustrated with respect to the embodiment described for testing device 20.

Figure 9:
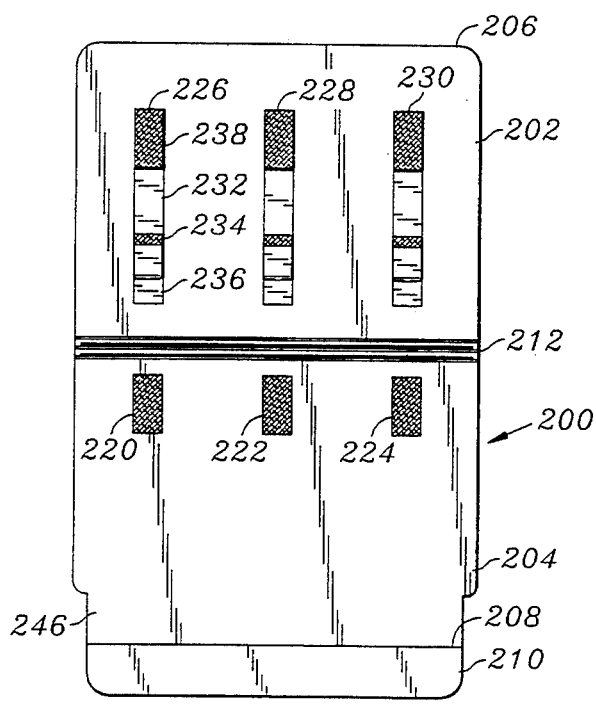
FIG. 9 is a view of another form of a testing device utilizing the bevel closure in accordance with the present invention.
Figure 10:
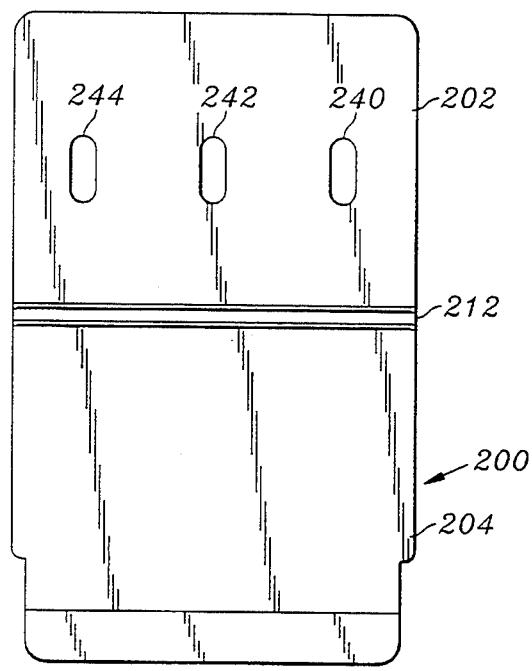
FIG. 10 is the opposite side of the device of FIG. 9.

Another form of a testing device employing the closure of the present invention is illustrated in FIGS. 9 and 10. Such a testing device 200, which may be suitable for testing of hemoglobin in, for example, fecal specimens, includes a front panel 202 and a back panel 204. A closure in accordance with the present invention is formed by a beveled edge 206 formed at an outer edge of the front panel 202 and an undercut edge 208 on a fixed member 210. A hinge 212 is defined between the front and back panels 202, 204.

A plurality of sample application pads 220, 222, 224 are disposed on the inside of the back panel 204 proximate the hinge 212, and a corresponding plurality of chromatographic testing members 226, 228, 230 are disposed on the inside of the front panel 202. Each of the testing members 226, 228, 230 includes a chromatographic membrane 232, a labeled reagent pad 234, a transfer pad 236 aligned so as to contact a corresponding sample application pad (such as pad 220) when the testing device 200 is closed, and an absorbent pad 238 at a second end of the chromatographic member 232.

Windows 240, 242, 246 are formed in the front panel 202 in alignment with the chromatographic testing members 226, 228, 230 so as to allow observation of test results. A reduced width portion 246 of the back panel 204 allows the front panel 202 to be easily lifted away from the back panel 204 to open the testing device 200.

In use, the testing device 200 is opened, samples that may contain an analyte of interest, such as hemoglobin, are applied to the sample application pads 220, 222, 224, and the device is closed by pressing the front and back panels 202, 204 together, thus engaging the beveled edge 206 beneath the undercut edge 208. The samples flow through the chromatographic testing members 226, 228, 230, performing, for example, an immunochemical analysis of the samples to thereby indicate the presence or absence of hemoglobin in the samples. Presence of hemoglobin may be indicated by means of visible lines appearing in windows 240, 242, 244. Such a testing device is similar to the hemoglobin testing device described in the above-referenced U.S. patent application Ser. No. 07/888,831. The testing device 200 may be formed in a manner and process similar to that described above with respect to the testing device 20, and in the embodiment of the testing device 200 of FIGS. 9 and 10.

Another embodiment of a testing device incorporating the closure of the present invention is illustrated in FIG. 11. A testing device 300 includes a front panel 302 and a back panel 304 joined by a hinge 306. Closures in accordance with the present invention are formed by beveled edges 308, 310 on opposite edges of the front panel 302, and corresponding undercut edges 312, 314 formed by corresponding planar fixed members 316, 318 which are proximate corresponding edges of the back panel 304. As a further alternative, the hinge 306 may be eliminated, thus enabling the front panel 302 to be completely removable from the device 300. In either embodiment, such a testing device may include testing elements (not shown) for sample analysis.

A further alternative of a device in accordance with the present invention is a device 340 of FIG. 12. The device 340 includes a front panel 342, a back panel 344 (seen by way of a cut away portion of the front panel 342 in FIG. 12). The front and back panels 342, 344 are joined at a hinge 346. A first and second closure 348, 350, both as described above with reference to the other embodiments disclosed herein, meet at a right angle 352. The device 340 may include testing elements similar to those described with respect to the testing device 20 and the testing device 200, or other testing elements.

Another form of the present invention is illustrated in FIG. 13, wherein a device 360 is similar to the device of FIG. 1, including a front panel 362, back panel 364, and a closure in accordance with the present invention defined by a beveled edge 366 and an undercut edge 368. A portion 370 of the front panel 362 extends beyond the beveled edge 366, thus hiding the closure formed by the edges 366, 368 when the front and back panels 362, 364 are closed.

Additional alternatives of a closure in accordance with the present invention are illustrated in FIGS. 14A–14C. A closure 400 formed by a fixed or retaining member 402 and a movable or retained member 404 includes an angled portion 406 and a perpendicular portion 408 that is perpendicular to a base member 410. In FIG. 14B, a closure 420 is formed by a fixed or retaining member 422 and a movable or retained member 424 that includes an angled portion 426 proximate a base member 428 and a perpendicular portion 430. In the embodiment of FIG. 14B, the fixed or retaining member 422 includes a double beveled edge 432, although a single bevel and a perpendicular portion corresponding to the perpendicular portion 430 would also be suitable.

With respect to FIG. 14C, a first member 440 includes a double angled edge having angled surfaces 442 and 444. A second member 446 with a double beveled edge having surfaces 448, 450 may be retained by the angled surfaces 442, 444.

It is to be appreciated that the embodiments of FIGS. 14A and 14B do not require the base member 410 and the base member 428, respectively, if further displacement of the movable or retained members 404 and 428 downwardly as viewed in FIGS. 14A and 14B is not important. Further, the embodiment of 14C enables the second member 446 to be captured by the first member 440 (or vice versa) regardless of whether the second member 446 approaches the first member 440 from above or below the first member 440 as viewed with respect to FIG. 14C. It is to be appreciated that "above" and "below" as used in the description of the embodiments of FIGS. 14A, 14B and 14C are relative with respect to such Figures and should not be deemed as limitations with respect to the design or operability of the present invention.

Figure 15:
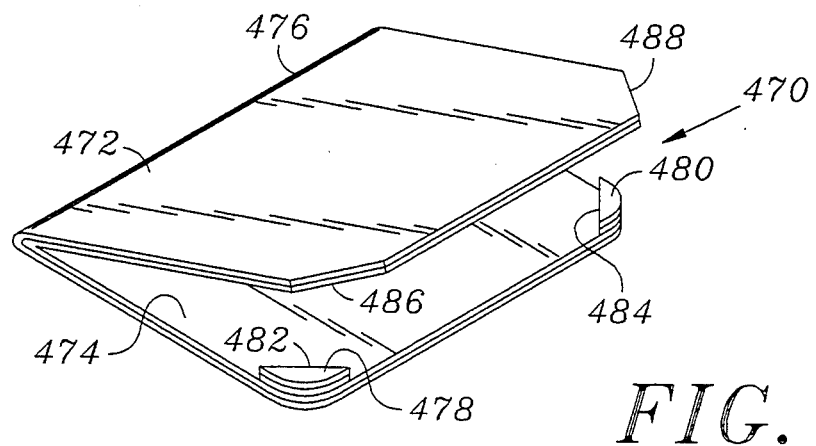
FIG. 15 is another device in accordance with the present invention.

Another embodiment of a device according to the present invention is shown in FIG. 15. Such a device 470 includes a cover 472 and base 474 joined by a hinge 476. Outer corners of the base 474 include retaining members 478, 480 that include undercut edges 482, 484. Corresponding beveled edges 486, 488 at corresponding corners of the cover 472 cooperate with the undercut edges to form a closure in accordance with the present invention. The device 470 may include testing elements similar to those described above.

An advantage of the closure of the present invention, particularly with respect to testing devices and devices as described herein, is that the closing force is equally distributed along the length of the closure, such as the closure 40 in the testing device 20. This is to be compared with, for example, closing techniques such as strips of peelable tape, hook-and-loop fasteners, snaps and tabs.

Various alternatives are within the scope of the present invention. For example, although the devices disclosed herein are described with respect to SBS paper board material, other materials may also be used, such as plastic. Further, a single material thicknesses of material or more than two thicknesses are also useable, rather than the two thicknesses of material for the devices. Additionally, a closure in accordance with the present invention can be curved or curving in addition to the straight or linear closures disclosed herein. Also, the closure in accordance with the present invention can be used on other than test devices, such as on envelopes, boxes, other containers, and the like. Other suitable means from positioning, for example, the front and back panels 22, 24 of the device 20 include other forms of mechanical hinges or hinges formed separately from the device and affixed to the device to provide the positioning function, and other flexible materials such a tape.

Although particular embodiments of a closure and devices using such a closure are described herein, the present invention is not to be limited by such specific embodiments, but is to be afforded the full scope of the appended claims and all equivalents thereto.

I claim:

1. A reclosable testing device, comprising:
   a base member;
   a cover member;
   a fixed member fixed to the base member, the fixed member having an undercut edge;
   a hinge between the base member and cover member;
   a testing element fixed to at least one of the base member or the cover member; and,
   closure means comprising a beveled edge on the cover member, the beveled edge being supplementary to the undercut edge and being adapted to be received and retained in a closed position with the undercut edge of the fixed member in an edge-to-edge to-edge engagement, the base member, cover member, and fixed member being formed of a sufficiently rigid material to minimize bowing on the closure thereby to ensure that a sample for testing and the testing element come into operative contact for effecting a test, and that a force is distributed substantially evenly over the cover member, and thereby further ensuring that, together with the hinge between the base member and the cover member, and with the closure means, the closure force is substantially equally distributed along the length of the closure means.

2. A device as in claim 1, wherein the device further includes testing elements fixed to the base member.

3. A device as in claim 1, wherein the device further includes testing elements fixed to the cover member.

4. A device as claimed in claim 1, wherein the cover member and fixed member extend respectively between extremities defined between ends, the beveled edge on the cover member extending from about one end of the cover member to about the opposite end of the cover member, and the supplementary undercut edge extending from about one end of the fixed member to about the opposite end of the fixed member.

5. A device as claimed in claim 1, including a testing element fixed to the base member and a testing element fixed to the cover member, whereby when the beveled edge is in a closed position there is a closure force for effecting transfer of a fluid between the test elements, and wherein the beveled edge and the supplementary undercut edge are positioned in a line from the hinge at least about opposite the test elements where the fluid transfers between the test elements.

6. A device as claimed in claim 1, including an extension portion of the cover member extending beyond the beveled edge, the extending portion covering a line of closure formed by the beveled edge and the undercut edge when the cover member and the fixed member are closed.

7. A device as in claim 1, wherein the device further includes first testing elements fixed to the base member and second testing elements fixed to the cover member.

8. A device as in claim 7, wherein the first and second testing elements are opposable when the cover member is closed and retained by the closure means.

9. A device as in claim 8, wherein either the first testing elements or the second testing elements include a chromatographic medium.

10. A reclosable testing device, comprising:
    a base member;
    a cover member;
    fixed members fixed to the base member, each fixed member having an undercut edge; a hinge between the base member and cover member;
    a testing element fixed to at least one of the base member or the cover member; and,
    closure means comprising beveled edges on the cover member, the beveled edges being supplementary to the undercut edges and being adapted to be received and retained in a closed position with the undercut edges of the fixed member in an edge-toedge engagement, the base member, cover member, and fixed member being formed of a sufficiently rigid material to minimize bowing on the closure thereby to ensure that a sample for testing and the testing element come into operative contact for effecting a test, and that a force is distributed substantially evenly over the cover member, and thereby further ensuring that, together with the hinge between the base member and the cover member, and with the closure means, the closure force is substantially equally distributed along the length of the closure means.

11. A device as claimed in claim 10, including a testing element fixed to the base member and a testing element fixed to the cover member, whereby when the beveled edge is in a closed position there is a closure force for effecting transfer of a fluid between the testing elements, and including a hinge between the base member and cover member, wherein at least one portion of the beveled edge and one portion of the undercut edge are positioned in a line from the hinge at least about opposite the test elements where the fluid transfers between the test elements, and another portion of the beveled edge and another portion of the undercut edge are located at a position removed from the elements where the fluid transfers between the test elements.

12. A device as claimed in claim 10, wherein the hinge between the base member and cover member, and wherein the fixed member and cover member respectively include corners remote from the hinge and wherein the undercut edges and the beveled edges respectively are located at the corners, and not between the respective corners.

13. A device as claimed in claim 10, wherein the hinge between the base member and cover member, and wherein the base member includes opposite ends directed transversely from the hinge, and includes a fixed member located at each respective end and the beveled edges are located respectively at the opposite ends, thereby to constitute closures on at least two sides of the device.

14. A device as claimed in claim 10, wherein the hinge between the base member and cover member, and wherein the base member includes an adjacent end directed traversely from the hinge, and a side opposite the hinge and the beveled edge and the undercut edge are located respectively at the adjacent end and the opposite end, thereby to constitute closures on at least two sides of the device.

15. A reclosable testing device, comprising:
a base member;
a cover member having a beveled edge;
a fixed member fixed to the base member, the fixed member having an undercut edge being supplementary to the beveled edge;
a hinge between the base member and cover member;
closure of the cover member on the base member effecting engagement of the beveled edge with the undercut edge of the fixed member, the beveled edge being adapted to be received and retained in a closed position in an edge-to-edge engagement with the undercut edge of the fixed member; and,
a testing element fixed to the base member and a testing element fixed to the cover member, the members being contact when the cover member and the base member are closed, the base member, cover member, and fixed member being formed of a sufficiently rigid material to minimize bowing on the closure thereby to ensure that a sample for testing and the testing element come into operative contact for effecting a test, and that a force is distributed substantially evenly over the cove; member, and thereby further ensuring that, together with the hinge between the base member and the cover member, and with the closure means, the closure force is substantially equally distributed along the length of the closure means.

16. A device as claimed in claim 15, wherein the cover member and fixed member extend respectively between extremities defined between ends, the beveled edge on the cover member extending from about one end of the cover member to about the opposite end of the cover member, and the supplementary undercut edge extending from about one end of the fixed member to about the opposite end of the fixed member.

17. A device as claimed in claim 15, wherein the beveled edge and the supplementary undercut edge are positioned in a line from the hinge at least about opposite the test elements.

18. A device as claimed in claim 15, including an extension portion of the cover member extending beyond the beveled edge, the extending portion covering a line of closure formed by the beveled edge and the undercut edge when the cover member and the fixed member are closed.

19. A reclosable testing device, comprising:
a base member;
a cover member having beveled edges;
fixed members fixed to the base member, the fixed members having undercut edges, a hinge between the base member and cover member the undercut edges being supplementary to the beveled edges such that in a closed position of the cover member and base member the beveled edge and the undercut edge are in edge-to-edge engagement;
a testing element fixed to the base member and a testing element fixed to the cover member, the members being in contact when the cover member and the base member are closed, the base member, cover member, and fixed member being formed of a sufficiently rigid material to minimize bowing on the closure, thereby to ensure that a sample for testing and the testing element come into operative contact for effecting a test, and that a force is distributed substantially evenly over the cover member and thereby further ensuring that, together with the hinge between the base member and the cover member, and with the closure means, the closure force is substantially equally distributed along the length of the closure means.

20. A device as claimed in claim 19, including a hinge between the base member and cover member, and wherein the base member includes opposite ends directed traversely from the hinge, and includes fixed members located at each respective end and the beveled edges and undercut edges are located respectively at the opposite ends, and including an elongated chromatographic medium with at least one of the elements for fluid to traverse the chromatographic medium from a first end towards a second end of the chromatographic medium.

21. A device as claimed in claim 19, including a hinge between the base member and cover member, and wherein the base member includes an adjacent end located transversely from the hinge, and including a side opposite the hinge, and the beveled edges and the undercut edges being located respectively at the adjacent end and the opposite side and including an elongated chromatographic medium with at least one of the test elements for fluid to traverse the chromatographic medium from a first end towards a second end of the chromatographic medium.

22. A device as claimed in claim 19, whereby when the beveled edge is in a closed position, a closure force is applied between the cover member and the fixed member, and including a hinge between the base member and cover member and wherein at least one portion of the beveled edge and one portion of the undercut edge are positioned in a line from the hinge at least about opposite the test elements and another portion of the beveled edge and another portion of the undercut edge are located at a position removed from the elements, and wherein one of the test elements includes an elongated chromatographic medium for fluid to traverse the chromatographic medium from a first end towards a second end of the chromatographic medium.

23. A device as claimed in claim 22, including a window located in at least one of the base member and cover member, the window being aligned along the length of the chromatographic medium such that a test indication on the chromatographic medium is visible through the window when the base member and cover member are in a closed position.

24. A device as claimed in claim 19, including a hinge between the base member and cover member wherein the fixed members and cover member respectively include corners remote from the hinge and wherein the undercut edges and the beveled edges are located at the corners and not between the respective corners, and including an elongated chromatographic medium with at least one of the elements for fluid to traverse the chromatographic medium from a first end towards a second end of the chromatographic medium.

25. A device as claimed in claim 24, including a window located in at least one of the base member and cover member, the window being aligned along the length of the chromatographic medium such that a test indication on the chromatographic medium is visible through the window when the base member and cover member are in a closed position.

26. A reclosable chromatographic testing device, comprising:

a base member;
a cover member;
a fixed member fixed to the base member, the fixed member having an undercut edge;
a hinge between the base member and cover member;
a testing element fixed to the base member, and a testing element fixed to the cover member, at least one of the testing elements including an elongated chromatographic medium, and wherein one of the testing elements is arranged for receiving fluid and for transferring the fluid to the testing element having the chromatographic medium whereby the fluid is arranged to traverse along the chromatographic medium from a first end of the medium towards a second end of the medium; and,
closure means comprising a beveled edge on the cover member, the beveled edge being supplementary to the undercut edge and being adapted to be received and retained in a closed position with the undercut edge of the fixed member in an edge-to-edge engagement, the base member, cover member, and fixed member being formed of a sufficiently rigid material to minimize bowing on the closure and thereby ensure that, together with the hinge between the base member and the cover member, and with the closure means, the closure force is substantially equally distributed along the length of the closure means whereby when the beveled edge is in the closed position, a closure force is distributed substantially uniformly between the cover member and the fixed member such that the fluid is effectively transferred between the testing elements and is enabled to effectively traverse the chromatographic medium.

27. A device as claimed in claim 26, including a window located in at least one of the base member and cover member, the window being aligned along the length of the chromatographic medium such that a test indication on the chromatographic medium is visible through the window when the base member and cover member are in a closed position.

28. A device as claimed in claim 26, wherein the undercut angle is less than about 90 degrees relative to a base.

29. A device as claimed in claim 26, wherein the base member and cover member are formed from a same board material element and the hinge includes at lease one crease formed in the board material, the board material having a thickness of about 0.024 inches.

30. A device as claimed in claim 26, wherein the base member and the cover member are planar elements formed from a same material element having a thickness and the hinge is formed along a crease line in the material and, the test elements are located in adjacency on the covered member and the base member and the fixed member is mounted on a portion of the base member, such that in a position of closure the cover portion overlies the portion of the base member not occupied by the fixed member, and the cover member and fixed members have edges in abutment, and wherein an inward force is applied by the cover member and the base member on the test elements substantially uniformly when the edge of the fixed member and the edge of the cover member are in the edge-to-edge engagement.

31. A reclosable chromatographic testing device, comprising:

a base member;
a cover member;
fixed members fixed to the base member, each fixed member having an undercut edge; a hinge between the base member and cover member;
a testing element fixed to the base member, and a testing element fixed to the cover member, at least one of the testing elements including an elongated chromatographic medium, and wherein one of the testing elements is arranged for receiving fluid and for transferring the fluid to the testing element having the chromatographic medium whereby the fluid is arranged to traverse along the chromatographic medium from a first end of the medium towards a second end of the medium; and,
closure means comprising beveled edges on the cover member, the beveled edges being supplementary to the undercut edges and being adapted to be received and retained in a closed position with the undercut edges of the fixed members in an edge-to-edge engagement, the base member, cover member, and fixed member being formed of a sufficiently rigid material to minimize bowing on the closure and thereby ensure that, together with the hinge between the base member and the cover member, and with the closure means, the closure force is substantially equally distributed along the length of the closure means whereby when the beveled edges are in the closed position, a closure force is distributed substantially uniformly between the cover member and the fixed members such that the fluid is effectively transferred between the testing elements and is enabled to effectively traverse the chromatographic medium.

32. A device as claimed in claim 31, including a window located in at least one of the base member and cover member, the window being aligned along the length of the chromatographic medium such that a test indication on the chromatographic medium is visible through the window when the base member and cover member are in a closed position.

33. A device as claimed in claim 31, wherein the undercut angle is less than about 90 degrees relative to a base.

34. A device as claimed in claim 31, including a hinge wherein the base member and cover member are formed from a same board material element and the hinge includes at lease one crease formed in the board material, the board material having a thickness of about 0.024 inches.

35. A device as claimed in claim 31, including a hinge wherein the base member and the cover member are planar elements formed from a same material element having a thickness and the hinge is formed along a crease line in the material and, the test elements are located in adjacency on the covered member and the base member and the fixed member is mounted on a portion of the base member, such that in a position of closure the cover portion overlies the portion of the base member not occupied by the fixed member, and the cover member and fixed members have edges in abutment, and wherein an inward force is applied by the cover member and the base member on the test elements towards each other is effected uniformly when the edge of the fixed member and the edge of the cover member are in the edge-to-edge engagement.

36. A reclosable testing device, comprising:
 a base member;
 a cover member having a beveled edge, the beveled edge including an exposed line of engagement;
 a fixed member fixed to the base member, the fixed member having an undercut edge being supplementary to the beveled edge and including an exposed line of engagement;
 a hinge between the base member and cover member;
 closure of the cover member on the base member effecting engagement of the beveled edge with the undercut edge, the beveled edge being adapted to be received and retained in a closed position in an edge-to-edge engagement with the undercut edge of the fixed member such that, the exposed lines of engagement of the beveled edge and the undercut edge respectively are substantially flush with the fixed member and cover member
 a testing element fixed to the base member and a testing element fixed to the cover member at least one of the testing elements being arranged for receiving fluid and for transferring the fluid to the testing element on the other testing element, and the beveled edge being adapted to be received and retained in a closed position in an edge-to-edge engagement with the undercut edge of the fixed member, the base member, cover member, and fixed member being formed of a sufficiently rigid material to minimize bowing on the closure thereby to ensure that a sample for testing and the testing element come into operative contact for effecting a test, and that a force is distributed substantially evenly over the cover member, and thereby further ensuring that, together with the hinge between the base member and the cover member, and with the closure means, the closure force is substantially equally distributed along the length of the closure means.

37. A device as claimed in claim 36, wherein the undercut angle is less than about 90 degrees relative to a base.

38. A device as claimed in claim 36, wherein the base member and cover member are formed from a same board material element and the hinge includes at lease one crease formed in the board material, the board material having a thickness of about 0.024 inches.

39. A device as claimed in claim 36, wherein the base member and the cover member are planar elements formed from a same material element having a thickness and the hinge is formed along a crease line in the material and, the test elements are located in adjacency on the covered member and the base member and the fixed member is mounted on a portion of the base member, such that in a position of closure the cover portion overlies the portion of the base member not occupied by the fixed member, and the cover member and fixed members have edges in abutment, and wherein an inward force is applied by the cover member and the base member on the test elements towards each other is effected uniformly when the edge of the fixed member and the edge of the cover member are in the edge-to-edge engagement.

40. A reclosable testing device, comprising:
 a base member;
 a cover member having beveled edges, the beveled edges including exposed lines of engagement;
 fixed members fixed to the base member, the fixed members having undercut edges the undercut edges being supplementary to the beveled edges and including exposed lines of engagement;
 a testing element fixed to the base member and a testing element fixed to the cover member, at least one of the testing elements being arranged for receiving fluid and for transferring the fluid to the testing element, and closure of the cover member on the base member effecting engagement of the beveled edges to be received and retained edge-to-edge contact in the closed position with the undercut edges of the fixed members and the exposed lines of engagement of the beveled edges and the undercut edges respectively being substantially flush with the fixed members and the cover member, the base member, cover member, and fixed member being formed of a sufficiently rigid material to minimize bowing on the closure thereby to ensure that a sample for testing and the testing element come into operative contact for effecting a test, and that a force is distributed substantially evenly over the cover member, and thereby further ensuring that, together with the hinge between the base member and the cover member, and with the closure means, the closure force is substantially equally distributed along the length of the closure means.

41. A device as claimed in claim 40, wherein the undercut angle is less than about 90 degrees relative to a base.

42. A device as claimed in claim 40, including a hinge wherein the base member and cover member are formed from a same board material element and the hinge includes at lease one crease formed in the board material, the board material having a thickness of about 0.024 inches.

43. A device as claimed in claim 40, including a hinge wherein the base member and the cover member are planar elements formed from a same material element having a thickness and the hinge is formed along a crease line in the material and, the test elements are located in adjacency on the covered member and the base member and the fixed member is mounted on a portion of the base member, such that in a position of closure the cover portion overlies the portion of the base member not occupied by the fixed member, and the cover member and fixed members have edges in abutment, and wherein an inward force is applied by the cover member and the base member on the test elements towards each other is effected uniformly when the edge of the fixed member and the edge of the cover member are in the edge-to-edge engagement.

* * * * *